(12) United States Patent  (10) Patent No.: US 9,060,892 B2
Oepen et al. (45) Date of Patent: Jun. 23, 2015

(54) STENT WITH INDEPENDENT STENT RINGS AND TRANSITIONAL ATTACHMENTS

(75) Inventors: Randolf Von Oepen, Los Altos Hills, CA (US); Lorcan James Coffey, Tuebingen (DE); Richard R. Newhauser, Redwood City, CA (US); Thomas Rieth, Hirrlingen (DE); Travis R. Yribarren, Campbell, CA (US)

(73) Assignee: ABBOTT LABORATORIES VASCULAR ENTERPRISES LIMITED, Dublin (IE)

( * ) Notice: Subject to any disclaimer, the term of this patent is extended or adjusted under 35 U.S.C. 154(b) by 472 days.

(21) Appl. No.: 13/063,911

(22) PCT Filed: Sep. 11, 2009

(86) PCT No.: PCT/US2009/056719
§ 371 (c)(1),
(2), (4) Date: May 31, 2011

(87) PCT Pub. No.: WO2010/030928
PCT Pub. Date: Mar. 18, 2010

(65) Prior Publication Data
US 2011/0224777 A1 Sep. 15, 2011

Related U.S. Application Data

(60) Provisional application No. 61/097,158, filed on Sep. 15, 2008.

(51) Int. Cl.
*A61F 2/06* (2013.01)
*A61F 2/915* (2013.01)
(Continued)

(52) U.S. Cl.
CPC . *A61F 2/915* (2013.01); *A61F 2/91* (2013.01); *A61F 2/95* (2013.01); *A61F 2/958* (2013.01);
(Continued)

(58) Field of Classification Search
CPC ............ A61F 2002/91583; A61F 2002/30019; A61F 2002/30484; A61F 2002/828; A61F 2002/826; A61F 2002/89; A61F 2002/915
USPC .............. 623/1.11, 1.15–1.16, 1.18–1.2, 1.23
See application file for complete search history.

(56) References Cited

U.S. PATENT DOCUMENTS 6,015,815 A 1/2000 Mollison
6,251,134 B1 * 6/2001 Alt et al. ...................... 623/1.16
(Continued)

FOREIGN PATENT DOCUMENTS

WO WO 2006/099449 9/2006
WO WO 2007/109621 9/2007
WO WO 2010/030928 3/2010

OTHER PUBLICATIONS

U.S. Appl. No. 61/097,158, filed Sep. 20, 2009, Oepen et al.

*Primary Examiner* — Katrina Stransky
*Assistant Examiner* — Kendra Obu
(74) *Attorney, Agent, or Firm* — Workman Nydegger; Jonathan D. Feuchtwang

(57) ABSTRACT

A vascular endoprosthesis (100, 200, 300, 400, 500, 600) includes a radially-expandable first segment and a radially expandable second segment. The vascular endoprosthesis further includes first and second coupling elements. The first coupling element extends from the proximal end of the first segment toward the distal end of the second segment, and the second coupling element extends from the distal end of the second segment toward the proximal end of the first segment. The first and second coupling elements cooperate one with another to couple the first and second segments together when the vascular endoprosthesis is in a delivery configuration and to decouple the first and second segments when the vascular endoprosthesis is in a deployed configuration.

20 Claims, 8 Drawing Sheets

(51) Int. Cl.
  *A61F 2/91* (2013.01)
  *A61F 2/89* (2013.01)
  *A61F 2/95* (2013.01)
  *A61F 2/958* (2013.01)
  *A61F 2/82* (2013.01)

(52) U.S. Cl.
  CPC . *A61F 2002/826* (2013.01); *A61F 2002/91591* (2013.01); *A61F 2210/0004* (2013.01); *A61F 2210/0014* (2013.01); *A61F 2250/0071* (2013.01); *A61F 2/89* (2013.01); *A61F 2210/0076* (2013.01)

(56) References Cited

U.S. PATENT DOCUMENTS

| | | | |
|---|---|---|---|
| 6,329,386 B1 | 12/2001 | Mollison | |
| 6,334,870 B1* | 1/2002 | Ehr et al. | 623/1.16 |
| 7,175,654 B2* | 2/2007 | Bonsignore et al. | 623/1.15 |
| 2002/0188347 A1* | 12/2002 | Mathis | 623/1.16 |
| 2003/0195609 A1 | 10/2003 | Berenstein et al. | |
| 2006/0069424 A1 | 3/2006 | Acosta et al. | |
| 2006/0195175 A1* | 8/2006 | Bregulla | 623/1.15 |
| 2007/0219612 A1* | 9/2007 | Andreas et al. | 623/1.11 |
| 2007/0293939 A1 | 12/2007 | Shrivastava et al. | |

* cited by examiner

STENT WITH INDEPENDENT STENT RINGS AND TRANSITIONAL ATTACHMENTS

CROSS REFERENCE

This application is a U.S. Nationalization of PCT Application Number PCT/US2009/056719, filed on Sep. 11, 2009 and entitled "STENT WITH INDEPENDENT STENT RINGS AND TRANSITIONAL ATTACHMENTS" which claims the benefit of, and priority to, U.S. Provisional Patent Application Ser. No. 61/097,158, filed on Sep. 15, 2008 and entitled "STENT WITH INDEPENDENT STENT RINGS AND TRANSITIONAL ATTACHMENTS," the entireties of which are incorporated herein by reference.

BACKGROUND OF THE INVENTION

1. The Field of the Invention

The present invention relates to a vascular endoprosthesis deliverable and deployable within a body vessel of a human or animal. More particularly, the invention relates to an interconnected segmented vascular endoprosthesis that includes decoupleable segments.

2. The Relevant Technology

Stents, grafts, and a variety of other endoprostheses are used in interventional procedures, such as for treating aneurysms, for lining or repairing vessel walls, for filtering or controlling fluid flow, and for expanding or scaffolding occluded or collapsed vessels. Such endoprostheses may be delivered and used in virtually any accessible body lumen of a human or animal, and may be deployed by any of a variety of recognized means. One recognized use for a vascular endoprosthesis is for the treatment of atherosclerotic stenosis in blood vessels. For example, after a patient undergoes a percutaneous transluminal coronary angioplasty or similar interventional procedure, a stent is often deployed at the treatment site to improve the results of the medical procedure and reduce the likelihood of restenosis.

To reduce the likelihood of restenosis, the stent may be configured to scaffold or support the treated blood vessel; if desired, the stent may also be loaded with a beneficial agent so as to act as a delivery platform to reduce restenosis or the like. Other suitable examples of medical conditions for which endoprostheses are an appropriate treatment include, but are not limited to, arterial aneurysms, venous aneurysms, coronary artery disease, peripheral artery disease, peripheral venous disease, chronic limb ischemia, blockage or occlusion of the bile duct, esophageal disease or blockage, defects or disease of the colon, tracheal disease or defect, blockage of the large bronchi, blockage or occlusion of the ureter, or blockage or occlusion of the urethra.

Some conventional stent designs may include a series of annular segments that may be connected in series by way of coupling elements. Typically, a vascular endoprosthesis, such as a stent, is delivered by a delivery sheath, such as a catheter, to a desired location or deployment site inside a body lumen of a vessel or other tubular organ. The intended deployment site may be difficult to access by a physician and often involves moving the delivery system through a tortuous luminal pathway that may involve various turns or curves. Thus, to allow advancement through the luminal pathway to the deployment site, a vascular endoprosthesis may need to flex or otherwise bend to traverse the various curves.

While flexing or bending during delivery to the deployment site, large axial or radial forces may be exerted on the vascular endoprosthesis. In order to withstand the forces exerted on the vascular endoprosthesis, the series of annular segments may be coupled together, thus providing additional support to the annular segments, which may help avoid a segment collapse or damage.

Once deployed, however, the coupling elements, in some applications, may be disadvantageous. For example, a vascular endoprosthesis deployed in a Superficial Femoral Artery (SFA) application undergoes longitudinal, bending, torsional, tensile and radial cyclical loading that may lead to fatigue failures in the segments after deployment. In particular, when the vascular endoprosthesis is forced to bend after being deployed, the coupling elements require the portions of the segment apposed to the outside of the curve to lengthen and the portions of the segment apposed to the inside of the curve to shorten.

Due to the fact that the segment may not expand evenly, the lengthening and shortening of the segments generally increases fatigue failures within the segments and/or the coupling elements. Current vascular endoprosthesis designs which are subjected to these forces often fail. Failure may result in crack formation and possible stent fracture. In the event of stent fracture, the sharp edges may puncture the vessel, muscle tissue, and/or cause bleeding. Consequently, the fractured stent may cause thrombus formation or blockage within the vessel.

One way to design a vascular endoprosthesis that is capable of withstanding the in vivo conditions after deployment is to not couple the annular segments of a vascular endoprosthesis together. This approach may, however, lead to difficulties with deploying the vascular endoprosthesis and create incomplete scaffolding. For example, during deployment, uncoupled annular segments may "jump" out of the delivery sheath in a way that creates an overly large gap between annular elements. A large gap between adjacent annular segments may result in insufficient vessel scaffolding. Moreover, due to the possibility that an uncoupled segment may "jump" out of the delivery sheath during deployment, the uncoupled segment may not interface with the body lumen wall in an effective way, again causing insufficient vessel scaffolding.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present invention provide systems, methods and devices configured to place an uncoupled segmented vascular endoprosthesis within a body lumen.

In one example embodiment, a vascular endoprosthesis includes a radially expandable first segment having a proximal end and a distal end and a radially expandable second segment have a proximal end and a distal end. The vascular endoprosthesis further includes first and second coupling elements. The first coupling element extends from the proximal end of the first segment toward the distal end of the second segment, and the second coupling element extends from the distal end of the second segment toward the proximal end of the first segment. The first and second coupling elements cooperate one with another to couple the first and second segments together when the vascular endoprosthesis is in a delivery configuration and to decouple the first and second segments when the vascular endoprosthesis is in a deployed configuration.

In another example, a vascular medical device includes a first and a second annular segment, both of which are radially expandable. The vascular medical device further includes a plurality of coupling elements that are disposed on the first and second annular segments. The plurality of coupling elements are operatively associated one with another to couple said first and second annular segments together until the first and second annular segments undergo a transition from a delivery configuration towards a deployed configuration.

Another example embodiment includes a medical device system that includes a tubular delivery sheath that has a proximal end and a distal end. The delivery sheath is configured to transport a vascular endoprosthesis that has a delivery configuration and a deployed configuration. While in the delivery configuration, a first segment and a second segment of a vascular endoprosthesis are coupled together, but when in the deployed configuration the first and second segments are decoupled. The medical device system further includes an actuator that is operatively associated with the delivery sheath to cause the vascular endoprosthesis to undergo a transition from the delivery configuration to the deployed configuration.

In another example, a method of placing a segmented vascular endoprosthesis inside a body lumen is disclosed. The method may include coupling segments of a segmented vascular endoprosthesis to form a delivery configuration. The method may further include moving said segmented vascular endoprosthesis to a deployment site while the vascular endoprosthesis is in the delivery configuration. Moreover, the method may include the step of uncoupling the segments of the segmented vascular endoprosthesis to form a deployed configuration.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Figure 1A:
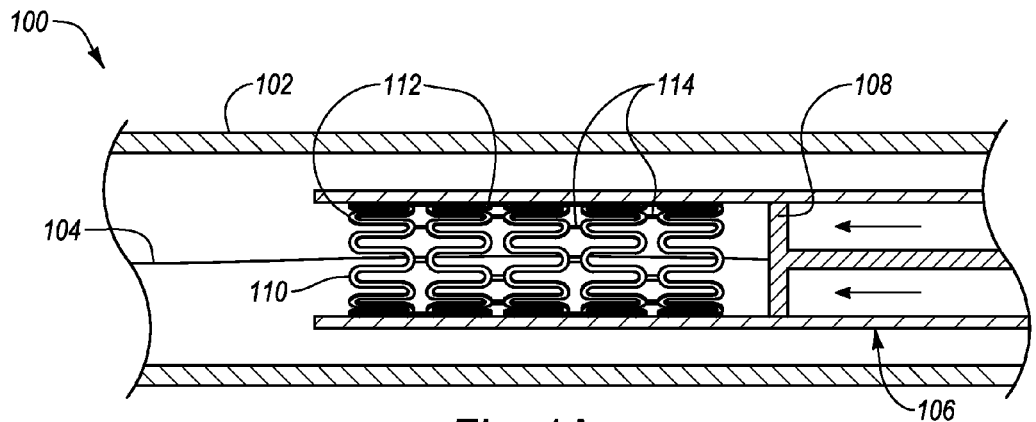
FIG. 1A illustrates a cross-sectional view of an example medical device system used to place a vascular endoprosthesis.

In general, the present invention relates to an implantable medical device such as a vascular endoprosthesis that is deliverable and deployable within a body lumen. More particularly, embodiments of the disclosure relate to a segmented implantable medical device that includes a plurality of decouplable annular segments. An example embodiment provides for an implantable medical device that has annular (or other configuration) segments that may be coupled during delivery into a body lumen, but the annular segments may decouple following deployment. Advantageously, the annular segments are independent and may prevent excessive gaps from occurring between the annular segments following deployment or after the segments are decoupled. Thus, the attachment between segments exists prior to deployment and the attachment or coupling between segments ceases to exist after deployment of the implantable medical device. Embodiments of the invention thus relate to a medical device that can better withstand the loading conditions due to radial, axial, and torsional strains of the deployment site.

I. Endoprostheses

FIG. 1 shows an example embodiment of a medical system, illustrated as a vascular endoprosthesis system 100. The vascular endoprosthesis system 100 functions within a body lumen 102, as shown in FIG. 1. A guide wire 104 is placed within the body lumen 102 such that the guide wire 104 may direct a delivery sheath 106 to a deployment site within the body lumen 102. The delivery sheath 106 may include an actuator 108 that is configured and associated with the delivery sheath 106 such that the actuator 108 and delivery sheath 106 may cooperate to deploy an implantable medical device from the delivery sheath 106. In this case, the vascular endoprosthesis system 100 includes a vascular endoprosthesis 110. The vascular endoprosthesis 110 is made up of a plurality of segments 112 that are coupled together by coupling elements 114.

Briefly, in operation, the guide wire 104 may be inserted into the body lumen 102. The delivery sheath 106 is able to track the guide wire 104 such that it may move through the body lumen 102 to a deployment site. While the delivery sheath is being moved through the body lumen 102, the segments 112 of the vascular endoprosthesis 110 are coupled together with coupling elements 114. The coupling elements 114 provide strength to the vascular endoprosthesis 110 that allow the vascular endoprosthesis 110 to be moved through a tortuous path within the body lumen 102 toward the deployment site without the vascular endoprosthesis 110 crushing while bending and flexing around curves and bends in the body lumen 102.

Upon reaching the deployment site within the body lumen 102, the delivery sheath 106 may begin a process of deploying the vascular endoprosthesis 110. In one example embodiment, the delivery sheath 106 cooperates with the actuator 108 to deploy the vascular endoprosthesis 110 by pushing or otherwise forcing the vascular endoprosthesis 110 out of the delivery sheath 106. Due to the coupling elements 114 that are coupling the segments 112 just before or during deployment, the segments 112 do not "jump" or spring out of the delivery sheath 106, but rather are restrained by the coupling elements 114.

Figure 1B:
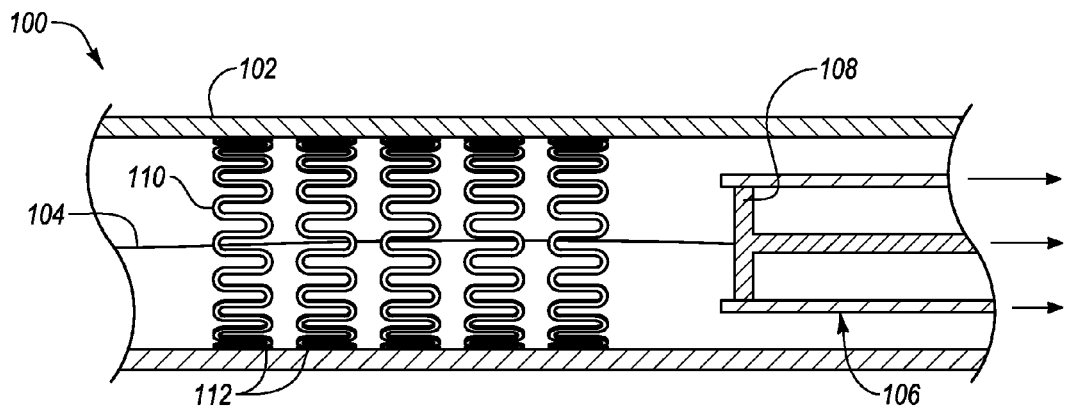
FIG. 1B illustrates a cross-sectional view of an example medical device that has been deployed in a body lumen.

As shown in FIG. 1B, upon deployment, the segments 112 of the vascular endoprosthesis 110 radially expand to engage the wall of the body lumen 102. Once the vascular endoprosthesis 110 is fully deployed, the coupling elements 114 are either disengaged from a coupled position such that the segments 112 of the deployed vascular endoprosthesis 110 are not coupled or connected with other segments 112 of the deployed vascular endoprosthesis. Disengaging the coupling elements can include instances where the coupling elements dissolve, bioerode, or biodegrade. For example, as shown in FIG. 1B, the coupling elements 114 do not appear because they may have dissolved, bioeroded, or biodegraded. In some embodiments, the coupling elements 114 can be selectively decoupled or disengaged. The delivery sheath 106 and the guide wire 104 are then withdrawn from the body lumen 102 after deployment.

Figure 1C:
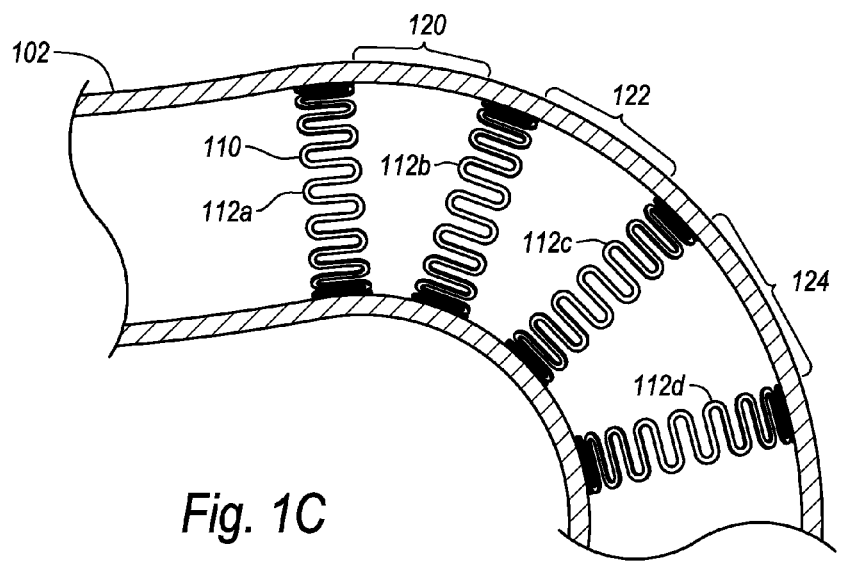
FIG. 1C illustrates a cross-sectional view of an example medical device that has been deployed in a body lumen that contains a curve.

FIG. 1C illustrates an example embodiment of the vascular endoprosthesis 110 in the deployed configuration within body lumen 102. Due to the decoupled nature of segments 112a-112d of the deployed vascular endoprosthesis 110, the vascular endoprosthesis 110 may be safely deployed in body lumens that curve or bend. In particular, and as illustrated in FIG. 1C, as the body lumen 102 curves, a first distance 120, measured between segment 112a and 112b, may be different than a second distance 122, measured between segment 112b and 112c. A third distance 124, measured between segment 112c and 112d, may be different from the first distance 120 and second distance 122. The decoupled nature of the segments 112a-112d in the deployed vascular endoprosthesis 110 provide for the variations in distances 120, 122, and 124 in the curved body lumen 102 since there are no coupling elements that require a particular distance between deployed segments. Thus, there is a reduced risk that the vascular endoprosthesis 110 fractures or is damaged within the bend in the body lumen 102.

The configuration of the vascular endoprosthesis system 100 shown in FIGS. 1A through 1C may vary from one embodiment to the next. For example, the specific deployment site at which the vascular endoprosthesis system 100 may be used may vary. In one example the body lumen 102 represents an artery such as the superficial femoral artery. In other embodiments body lumen 102 may represent various blood veins or various other lumens throughout a human or animal body.

The delivery sheath 106 is another aspect of the vascular endoprosthesis system 100 that may vary. As shown in FIG. 1A, the delivery sheath is made up of a tubular member that is designed to follow a guide wire 104. Example delivery sheaths 106 include catheters and introducer sheaths. Materials, configurations and characteristics of the delivery sheath 106 may vary from one embodiment to the next. For example, the delivery sheath 106 illustrated in FIGS. 1A and 1B has an actuator 108 that acts as a push rod that assists to deploy the vascular endoprosthesis 110. However, in other example embodiments the delivery sheath 106 may have various other actuator 108 configurations that are used to deploy the vascular endoprosthesis 110.

Just as the delivery sheath 106, the actuator 108 and the location of use of the vascular endoprosthesis system 100 may vary, so too may the vascular endoprosthesis 110 vary. FIGS. 2 through 6 illustrate various example embodiments of the vascular endoprosthesis 110 that provides for the segments 112 to be coupled in a delivery configuration and provides for the segments 112 to be decoupled in a deployed configuration.

Figure 2:
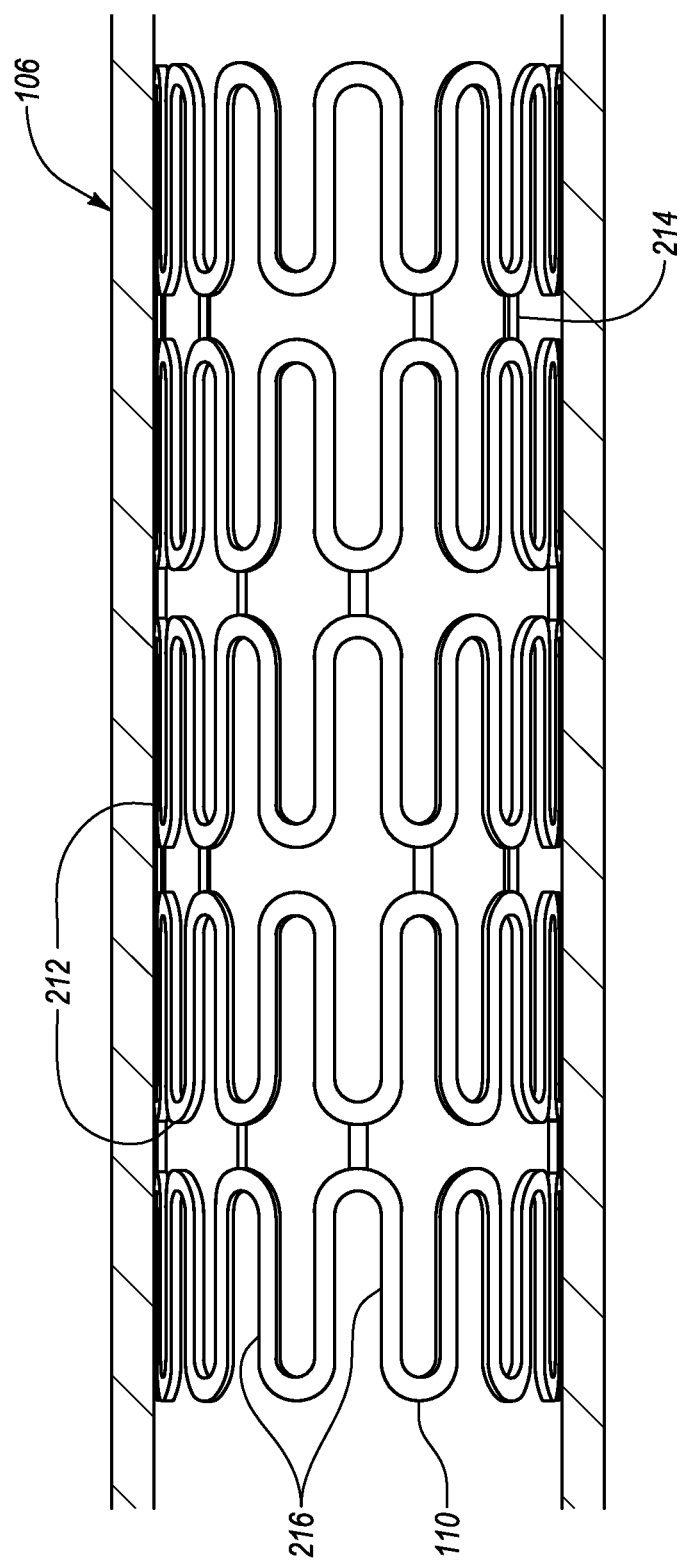
FIG. 2 illustrates a close-up view of an example medical device.

FIG. 2 illustrates a close up view of a vascular endoprosthesis 110 in a compressed or delivery configuration while inside of the delivery sheath 106. The vascular endoprosthesis 110 in the delivery configuration may include segments 212. Each of the segments 212 may consist of a plurality of struts 216 that may be formed to provide an expandable annular ring configuration for each segment 212. The struts 216 may have various configurations, for example, the struts 216 shown in FIG. 2 have a U-configuration, or in other words, two adjacent struts 216 are joined together to make a U-type shape. In other example embodiments, the struts 216 may have various other configurations. For example, a Z-configuration, a W-configuration, an N-configuration or any other configuration or combination of configurations may be used to produce the annular segments 212.

The particular strut 216 configurations allow segments 212 to be radially expandable such that they may be compressed into the delivery configuration within a delivery sheath 106, but upon deploying from the delivery sheath 106, the segments 212 may expand radially in order to interface with the body lumen 102 wall. For example, by altering the angle or distance defined between circumferentially-adjacent struts 216, the segments 212 may be radially expanded between a delivery configuration and a deployed configuration. The expandable structure may be expanded by the application of an external force, such as by a balloon, or by a change in delivery conditions, such as an increase in temperature, or the removal of a restraint, so as to allow the segments 212 to self expand. In some instances, the segments 212 may be shape set or have a shape memory at the deployed configuration. Thus, the segments 212 are compressed for delivery and then expand to the shape previously set during deployment.

Circumferentially-adjacent struts 216 of each segment 212 may be interconnected, either directly or indirectly, in an end-to-end format to define a continuous ring having a generally circular cross-sectional profile. However, in other example embodiments, the struts 216 may form a segment 212 with a C-type cross-sectional profile. Other cross-sectional profiles may also be used, as long as the cross-sectional profile is able to interface with the body lumen 102 to effectively support the body lumen 102 wall.

Not only may the struts 216 vary to form various cross-sectional profiles of the segments 212, but the actual cross-sectional configuration of the struts 216 may vary. In one example embodiment, the cross-sectional configuration of the struts 216 is generally circular. In other example embodiments, the struts 216 may have a cross-sectional configuration that is square, oval, trapezoidal, rectangular, or any other configuration or combination of configurations that would provide effective scaffolding for the body lumen 102.

In order to provide effective scaffolding, the number of segments 212 included in the vascular endoprosthesis 110 may vary from one embodiment to the next. For example, the number of segments may be determined by the length of body lumen 102 that needs treatment and/or the effective spacing of the segments in the treatment of the body lumen.

Depending on the type of treatment necessary, the vascular endoprosthesis 110 may also include various different sizes of segments 212. For example, the vascular endoprosthesis 110 may include a first segment with a first segment cross-sectional diameter and a second segment with a second segment cross-sectional diameter, the first segment cross-sectional diameter and the second segment cross-sectional diameter being different. Additionally, the vascular endoprosthesis 110 may include a plurality of sections, each section having a substantially constant segment cross-sectional diameter. Transition zones between each section may accommodate the transition from one section diameter to the next, such as to avoid an abrupt step from one section to the next. In this way, the vascular endoprosthesis may be configured to have various cross-sectional diameters to accommodate various treatments as necessary.

As illustrated in FIG. 2, another way in which the segments 212 may vary is in the way they are coupled together. Coupling elements 214 couple the segments 212 together in a delivery configuration. The coupling elements 214 may have various configurations from one embodiment to the next of the vascular endoprosthesis 110, or within the same embodiment. As illustrated in FIG. 2, the coupling elements 214 are connected to two struts 216 of adjacent segments 212 in such a way that the coupling elements 214 couple together the various segments 212 in a delivery configuration. Depending on the type of material used for the coupling elements, the coupling elements may be bonded to adjacent annular elements and, if necessary, to each other using welds or another metallurgical bond or with an adhesive.

During delivery of the vascular endoprosthesis 110 to the delivery site, the coupling elements 214 allow the vascular endoprosthesis 110 to move, when necessary, through the tortuous path of a body lumen to the delivery site within the body lumen. The coupling elements 214 support the segments 212 throughout delivery by providing the segments 212 with enough flexibility to bend and curve around corners, yet at the same time the coupling elements 214 provide sufficient strength reinforcement to avoid segment 212 crushing.

The coupling elements 214 may take various configurations and have various material properties, depending on the configuration of the vascular endoprosthesis 110. For example, the coupling elements 214 may be made of materials that are bioerodible, bioabsorbable, biodegradable, or bioresorbable. In one embodiment, the coupling elements 214 may be overmolded onto the segments 212 to bond the material to the segments 212. Alternatively, the coupling elements 214 could be mechanically coupled to the segments 212, such as by forming the coupling element 214 from a band that is wrapped around the crowns of adjacent segments 212. In this way, the coupling elements 214 may be made to couple the segments 212 during delivery, but uncouple the segments 212 after deployment by dissolving.

Bioerodible, bioabsorbable, biodegradable, or bioresorbable materials include, but are not limited to, metals such as magnesium, magnesium alloys, iron, and iron alloys, and polymers such as polylactic acid (also known as poly-L-lactic acid), polyglycolic acid, polyglactin, poly(dioxanone), poly (dioxanone), polyglyconate, copolymers of polyglycolic acid and $\epsilon$-caprolactam, and copolymers of lactic acid an $\epsilon$-caprolactam.

In particular, the coupling elements 214 may interconnect the segments 212 throughout the delivery process. Once the vascular endoprosthesis 110 is deployed within a body lumen 102, then the coupling elements 214 may be subject to a fluid, for example blood. The fluid may interact with the coupling elements 214 such that the bioerodible, bioabsorbable, biodegradable, or bioresorbable material dissolves in the fluid, thus allowing the coupling elements 214 to decouple from the segments 212. Once the coupling elements 214 are dissolved, the deployed vascular endoprosthesis 110 may include only decoupled segments within the body lumen, as illustrated in FIGS. 1B and 1C. Alternatively, the deployed vascular endoprosthesis 110 may include sections of decoupled segments in combination with sections of segments that remain coupled after deployment.

The number of coupling elements 214 may vary from one embodiment to the next, or may vary within the same embodiment. For example, in one embodiment, there may be three coupling elements 214 between each segment. In other example embodiments there may be more or less coupling elements 214. Moreover, the spacing of the coupling elements 214 around the segments 212 may vary from one embodiment to the next. For example, in an embodiment with three coupling elements 214 between each segment 212, the coupling elements 214 may be equally spaced around the segment 212. In another embodiment, the coupling elements 214 may be spaced to have unequal distances between them, or the coupling elements 214 may have a substantially random spacing. The number and/or spacing of the coupling elements 214 may also vary from one segment 212 to the next within the same vascular endoprosthesis 110.

Just as the number and spacing of the coupling elements 214 may vary, so too may the size of the coupling elements vary. The size of the coupling elements 214 may be determined based on the desired distance between segments 212 after deployment of the vascular endoprosthesis 110. For example, FIG. 2 illustrates an example vascular endoprosthesis 110 where the coupling elements are substantially all the same size. In other examples, the coupling elements 214 may vary in size from one segment to then next, or even from one coupling element 214 to the next between the same two segments 212.

In addition to having material properties that will allow the coupling elements 214 to decouple the segments 212 during deployment or shortly thereafter, the coupling elements 214 may also employ various mechanical configurations that provide for segment 212 decoupling when the vascular endoprosthesis 110 is in the deployed configuration. The endoprosthesis described in FIGS. 3A-6C may be functionally similar to the endoprosthesis previously described above. For instance, certain features will not be described in relation to the embodiments described with respect to FIGS. 3A-6C wherein those features may function in the manner as described above and are hereby incorporated into the alternative embodiments described below. Further, the example embodiments shown in FIGS. 3A-6C may include one or more aspects discussed with respect to the vascular endoprosthesis 110. In particular, the embodiments illustrated in FIGS. 3A through 6C may be example embodiments of the endoprosthesis 110 as described above.

Figure 3A:
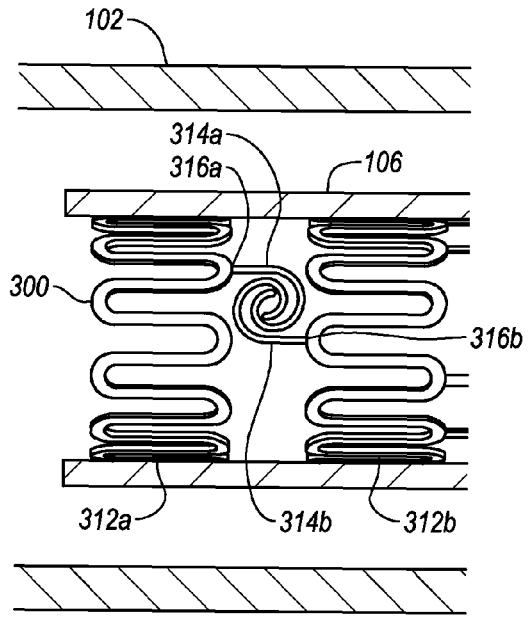
FIGS. 3A through 3C illustrate a cross-sectional view of an example medical device at various stages of an example deployment.

For example, FIGS. 3A-3D illustrate the deployment of an implantable medical device, such as the vascular endoprosthesis 300. As illustrated in FIG. 3A, a first coupling element 314a and a second coupling element 314b may have a spiral configuration. In particular, the first and second spiral coupling elements 314a and 314b are attached or otherwise joined with first and second struts 316a and 316b on first and second segments 312a and 312b, respectively. The first spiral coupling element 314a is interconnected, intertwined, or otherwise coupled to the second spiral coupling element 314b in a way that couples the first segment 312a to the second segment 312b during the delivery of the vascular endoprosthesis 300 to the deployment site.

Figure 3B:
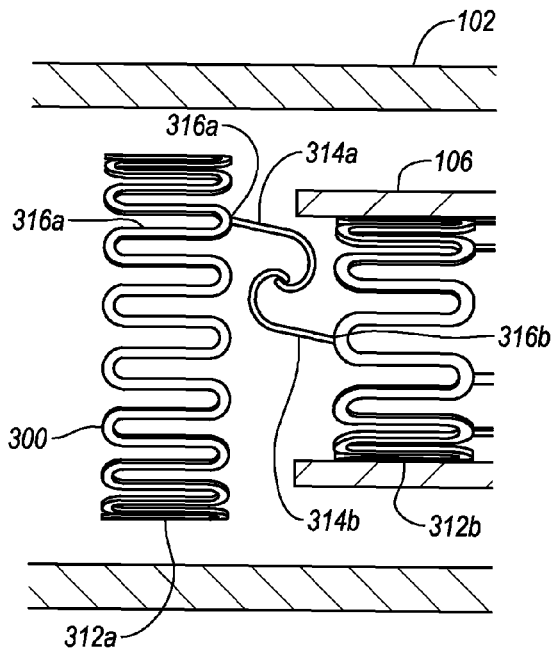

Upon reaching the deployment site, as shown in FIG. 3B, the vascular endoprosthesis 300 is deployed from the delivery sheath 106. During deployment, the first and second spiral coupling elements 314a and 314b may be configured to remain interconnected while the first segment 312a is deployed, thus, preventing the first segment 312a from jumping or otherwise springing out of the delivery sheath 106 in a way that would cause unequal, excessive, undesired, or unacceptable separation between the first and second segments 312a and 312b after deployment. For example, the first and second spiral coupling elements 314a and 314b may be located on the first and second segments 312a and 312b, respectively, in such a way that during the initial deployment of the first segment 312a from the delivery sheath 106, the first and second spiral coupling elements 314a and 314b remain interconnected, as shown in FIG. 3B, thus preventing the first segment 312a from "jumping" from the delivery sheath 106.

Figure 3C:
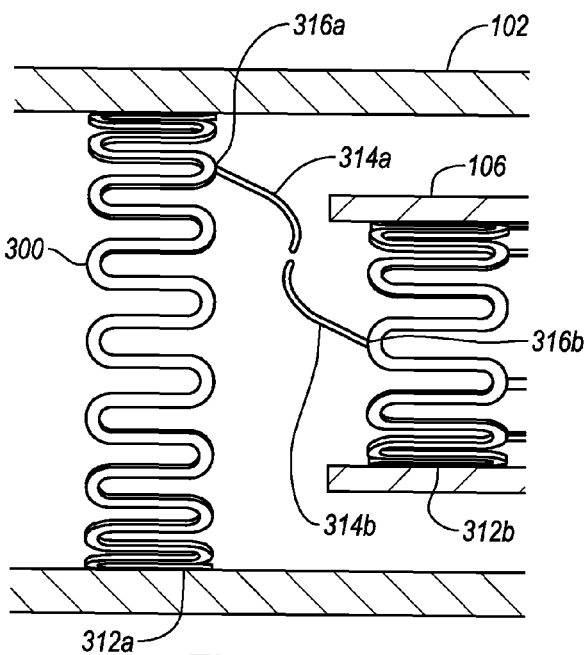

Further along in the deployment of first segment 312a, i.e., upon further radial expansion of first segment 312a, the first and second spiral coupling elements 314a and 314b may be positioned and sized such that the interconnecting portion of the spiral coupling elements 314a and 314b may be pulled in a way that unwinds and releases the interconnection between the first and second spiral coupling elements 314a and 314b, as illustrated in FIG. 3C. In particular, when first segment 312a is fully expanded, and second segment 312b is fully compressed, the distance created between the first and second spiral coupling elements 314a and 314b is such that the first and second spiral coupling elements 314a and 314b unwind and release from one another. Thus, as each new segment is introduced in the body lumen, the segments automatically decouple one at a time upon deployment.

In one embodiment, the first and second spiral coupling elements 314a and 314b may be formed from a shape memory alloy (SMA). One characteristic of SMAs that may be used to manufacture vascular endoprosthesis is that their shape may change as a result of a temperature transition. As such, in one embodiment, the decoupling of the first and second spiral coupling elements 314a and 314b may occur as a result of a temperature change upon deployment of the vascular endoprosthesis 300 in a body lumen. That is, the vascular endoprosthesis 300, and the spiral coupling elements 314a and 314b in particular, may be shape-set such that a shape change occurs at or near physiological temperature that results in the decoupling or unwinding of the first and second spiral coupling elements 314a and 314b upon deployment or shortly thereafter. There is no need for the spiral coupling elements 314a and 314b and the segments 312a and 312b to comprise different materials. For example, the entire structure could be Nitinol. However, if desired, the spiral coupling elements 314a and 314b may be made of an material such as Nitinol, for example, that can be welded to other materials such as stainless steel.

Further discussion of SMAs that experience a shape change at or near physiological temperature may be found in U.S. patent application Ser. No. 11/748,214 to Shrivastava and Kang entitled "FATIGUE RESISTANT ENDOPROSTHESES," the entirety of which is incorporated herein by reference in its entirety.

Another way in which the first and second spiral coupling elements 314a and 314b may decouple is that upon radial expansion of the first segment 312a, the spiral coupling elements 314a and 314b twist or turn relative to one another, thus unwinding the interconnection between the first and second spiral coupling elements 314a and 314b. For example, the first spiral coupling element 314a may be positioned on the first strut 316a such that upon expansion of first segment 312a, the first spiral coupling element 314a twists or turns relative to the second spiral coupling element 314b. Thus, upon twisting or turning relative to one another, the first and second spiral coupling elements 314a and 314b disengage.

Of course, the disengagement or the decoupling of the first and second spiral coupling elements 314a and 314b may take place after the first and second segments 312a and 312b are fully deployed. For example, the first and second spiral coupling elements 314a and 314b may be configured to remain interconnected throughout the deployment process and even after deployment. After deployment, however, the spiral coupling elements 314a and 314b may dissolve within the body lumen, thus, producing a segmented, decoupled vascular endoprosthesis within the body lumen (i.e., the spiral coupling elements 314a and 314b may be made from a bioerodible, bioabsorbable, biodegradable, or bioresorbable material).

In addition to the way in which the first and second spiral coupling elements 314a and 314b may couple during delivery, it should be noted that the interconnection between spiral element 314a and the spiral element 314b may be further facilitated by forming a shape in the side wall of the first and second spiral segments 312a and 312b. The shape in the side wall may provide a compact and smooth interconnection between the first and second spiral coupling elements 314a and 314b. For example, FIG. 3D shows that first segment 312a may have an angle formed in the side wall that is complimentary to an angle formed in the adjacent side wall of second segment 312b.

Figure 3D:
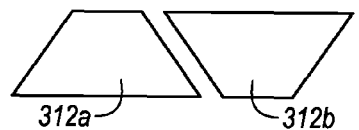
FIG. 3D illustrates an example cross-sectional side view of an example side wall configuration of example coupling elements.

The complimentary angles in the side walls of the first and second segments 312a and 312b may provide a more compact and secure structure to the overall vascular endoprosthesis 300 since the angled side walls in first segment 312a and second segment 312b allow the first and second segments 312a and 312b to overlap, as illustrated in FIG. 3D. In particular, because the angled side walls in first and second segments 312a and 312b may permit the overlapping, the first and second segment 312a and 312b may be configured to be closer in proximity with one another while positioned in the delivery configuration, thus creating a more compact configuration. Moreover, the overlapping may also provide additional strength because the first and second segments 312a and 312b may support one another while moving through the potentially tortuous vascular path to reach the deployment site.

The side wall configuration of the first and second segments 312a and 312b illustrated in FIG. 3D, or other equivalent configurations, may be obtained by laser cutting the first and second segments 312a and 312b from the same piece of material with a predetermined laser cutting pattern. Then, before coupling the first and second segments 312a and 312b together, second segment 312b may be turned inside out such that the angles formed in the side wall of second segment 312b during laser cutting may be complimentary to the angles in the side wall of the first segment 312a. In the case that the first and second spiral coupling elements 314a and 314b are also made from the same piece of material as the first and second segments 312a and 312b, then the angles between the side walls of the first and second spiral coupling elements 314a and 314b may likewise be complimentary. This manufacturing technique may be utilized in any of the embodiments that were described before or that will be described hereafter.

In addition to the various example embodiments discussed with reference to FIGS. 3A through 3D, FIGS. 4A through 4C illustrate another example embodiment of first and second coupling elements that may be coupled in the delivery configuration of the vascular endoprosthesis 400, but decoupled in the deployed configuration. The endoprosthesis 410 is another example of the endoprosthesis 110 and may have the same or similar structure as endoprosthesis 110, as discussed above. In particular, the vascular endoprosthesis 400 illustrated in FIG. 4A has a first segment 412a and a second segment 412b. The first segment 412a includes a ball coupling element 414a that is disposed on a first strut 416a. The second segment 412b includes a socket coupling element 414b that is disposed on a second strut 416b. The ball coupling element 414a and the socket coupling element 414b are configured such that the ball coupling element 414a may be received by and joined to the socket coupling element 414b. Thus, the first segment 412a and second segment 412b are coupled together by the ball coupling element 414a and socket coupling element 414b.

As with the previously discussed embodiments, the ball and socket coupling elements 414a and 414b allow for flexibility and strength between the segments of the vascular endoprosthesis 400 while in a delivery configuration within the delivery sheath 106. Upon realizing a deployed configuration, however, the ball and socket coupling elements 414a and 414b are able to decouple.

Figure 4A:
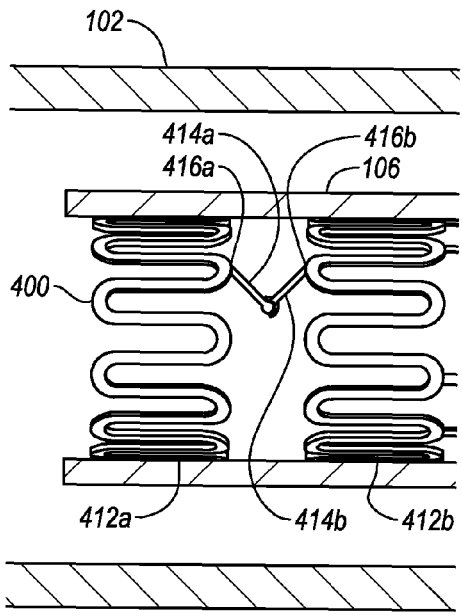
FIGS. 4A through 4C illustrate a cross-sectional view of an example medical device at various stages of an example deployment.
Figure 4B:
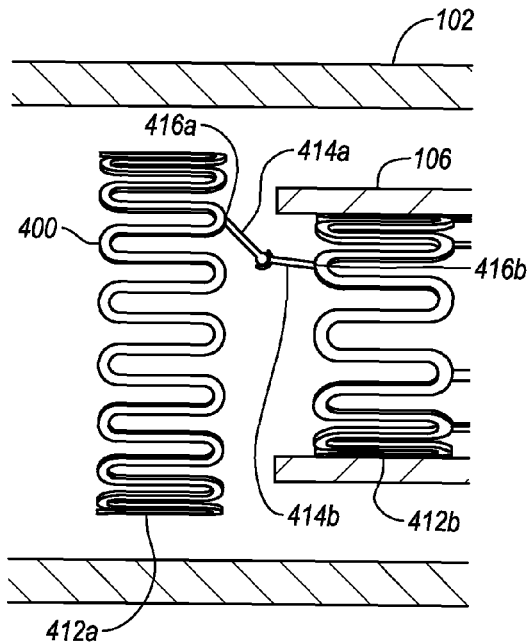
Figure 4C:
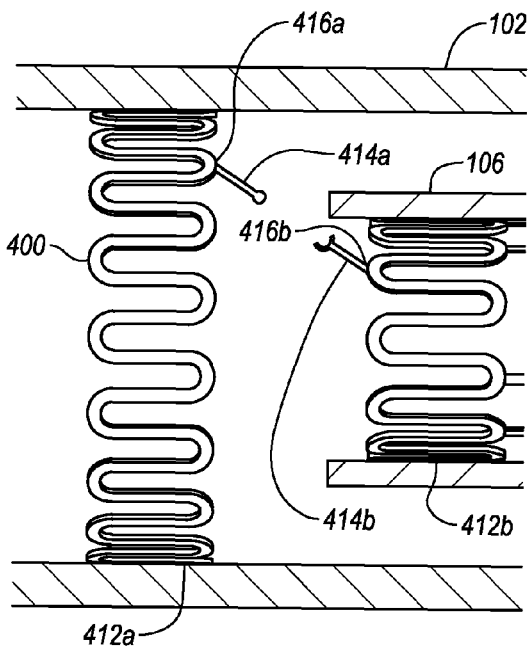

There are various ways in which the ball and socket coupling elements 414a and 414b may be configured to allow for the decoupling upon or shortly after deployment of a particular segment. For example, FIGS. 4B and 4C illustrate one example deployment process of an individual segment utilizing the ball and socket coupling elements 414a and 414b. In particular, FIG. 4B illustrates an example vascular endoprosthesis 400 during deployment of first segment 412a. As illustrated, segment 412a has been initially deployed from the delivery sheath 106 and has started to expand radially towards the body lumen 102 wall. At this point, the ball and socket coupling elements 414a and 414b are still connected, thus not allowing the first segment 412a to "jump" out of the delivery sheath. As the first segment 412a expands, the ball coupling element 414a pulls away from the socket coupling element 414b such that the ball coupling element 414a and socket coupling element 414b transition from a bended V-type configuration (shown in FIG. 4A) to a straight configuration shown in FIG. 4B.

In order to facilitate the transition from a V-type configuration to a straight configuration, both the ball coupling element 414a and the socket coupling element 414b may be attached to struts 416a and 416b, respectively, in such a way that the ball coupling element 414a and the socket coupling element 414b may pivot slightly (e.g., the ball and socket coupling elements 414a and 414b may be permitted to bend at the intersection of the coupling elements and their respective struts). Moreover, the ball portion of the ball coupling element 414a may interface with the socket portion of the socket coupling element 414b in a way that the ball portion may rotate within the socket portion. Thus, upon the segment 412a being initially deployed and expanding towards the body lumen 102 wall, the ball coupling element 414a and the socket coupling element 414b may transition from the delivery configuration towards the deployed configuration, or in other words, from a bent configuration to a straight configuration.

FIG. 4C shows an example where the first segment 412a has fully expanded and interfaced with the body lumen 102 wall, while second segment 412b is still located within the delivery sheath 106. As shown in FIG. 4C, the ball coupling element 414a and the socket coupling element 414b may be positioned and configured on their respective segments 412a and 412b in a way that when segment 412a is completely expanded, the ball coupling element 414a is able to pull away from, or be released by, the socket coupling element 414b. Thus, as the vascular endoprosthesis 110 is deployed segment by segment within the body lumen 102, the ball and socket coupling elements 414a and 414b remain coupled while in the delivery sheath 106 and upon initial deployment, but become uncoupled after full deployment. It is important to note that during deployment, as shown in FIG. 4B, the ball coupling element 414a may be still connected to, or coupled with, the socket coupling element 414b, thus, restricting the segment 412a from "jumping" or snapping out of the delivery sheath 106 in a way that would cause uneven, undesired, or unacceptable separation between the first and second segments 412a and 412b.

Another way in which the ball coupling element 414a may pull away from, or be released by, the socket coupling element 414b may be to have the socket portion of the socket coupling element 414b made from an SMA that changes the socket configuration. For example, the socket portion of the socket coupling element 414b may change from a closed or connected configuration to an open or release configuration upon experiencing a temperature transition within the body lumen. Therefore, upon or after deployment, the socket portion of the socket coupling element 414b may open to release the ball portion of the ball coupling element 414a.

Likewise, and as has been explained with previous embodiments, the ball coupling element 414a and socket coupling element 414b may remain connected after deployment of both the first segment 412a and the second segment 412b. However, the ball coupling element 414a and the socket coupling element 414b may be made from a material that is bioerodible, bioabsorbable, biodegradable, or bioresorbable such as to decouple after full deployment. For example, the ball portion and/or the socket portion of the ball and socket coupling elements 414a and 414b may be made out of a dissolvable material such that the interconnection between the ball and socket portion dissolves. Alternatively, the entire portion of the ball and/or socket coupling elements may be made from a dissolvable material.

Figure 5A:
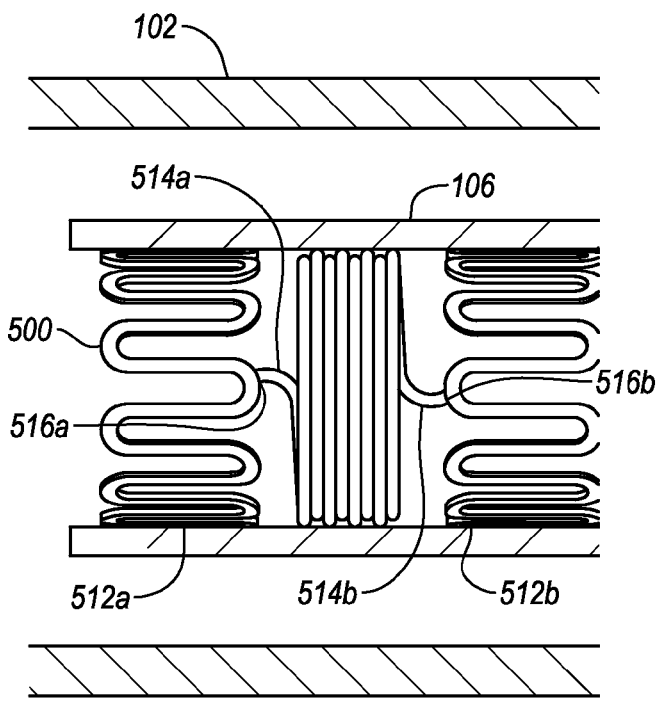
FIGS. 5A through 5C illustrate a cross-sectional view of an example medical device at various stages of an example deployment.

FIGS. 5A-5D illustrate another embodiment of a vascular endoprosthesis 500, which may be an example of the vascular endoprosthesis 110, as discussed above. In the vascular endoprosthesis 500, shown in FIG. 5A, coil coupling elements 514a and 514b may be configured in an interconnecting coil configuration. For example, as illustrated in FIG. 5A, first and second segments 512a and 512b may be coupled together with the coil coupling elements 514a and 514b. As more clearly illustrated in FIG. 5D, coil coupling elements 514a and 514b include interconnecting coil elements such that the coil elements of coil coupling element 514a interconnect or interface with the coil elements of coil coupling element 514b. For example, the interface between the coil coupling elements 514a and 514b may be understood as two springs that are pressed into each other laterally such that the coils of the two springs interconnect and create a coupling that resists decoupling in a direction perpendicular to the lateral direction from which the spring coils were joined.

The coil coupling configuration shown in FIGS. 5A through 5D is advantageous because the nature of the coupling as described above allows the coil coupling elements 514a and 514b to remain coupled upon experiencing the "jumping" force, which is generally directed parallel to the body lumen 102 path, while at the same time allowing for decoupling upon experiencing the radially expanding force, which is generally directed perpendicular to the body lumen 102 path. As with the previously discussed embodiments, this configuration of the coil coupling elements 514a and 514b allows the first and second segments 512a and 512b to remain coupled together while in a delivery configuration within the delivery sheath 106. Yet, upon deployment, the first and second segments 512a and 512b may decouple.

Figure 5B:
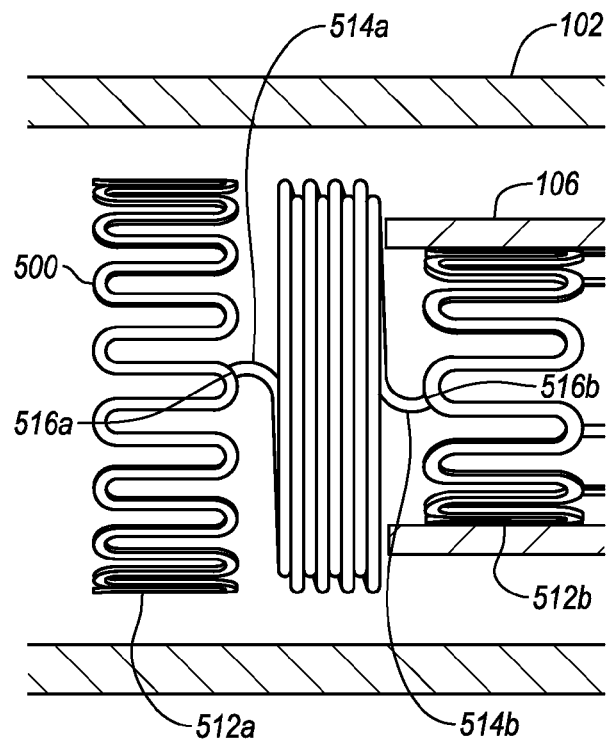
Figure 5C:
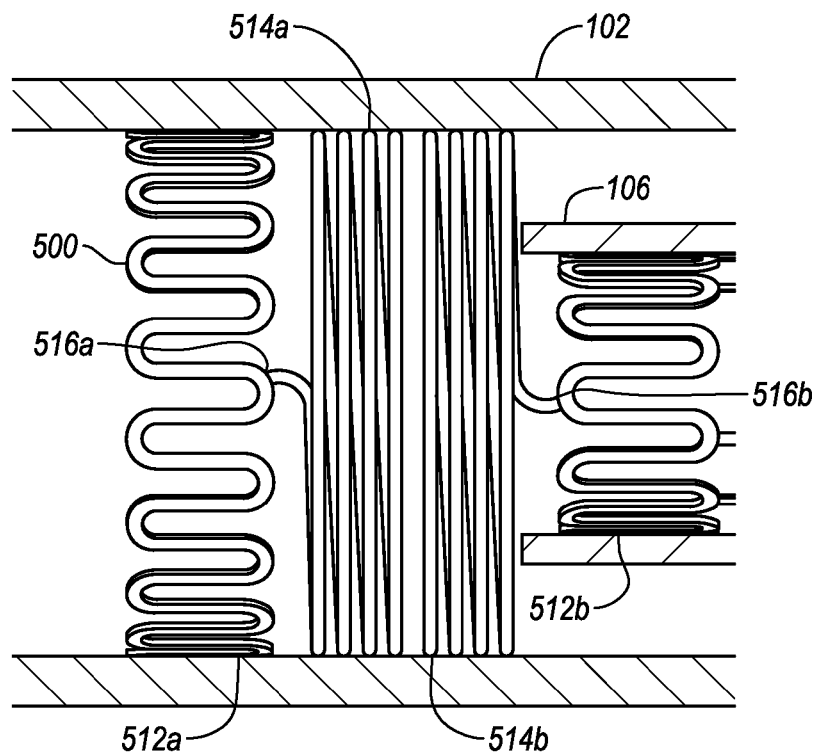
Figure 5D:
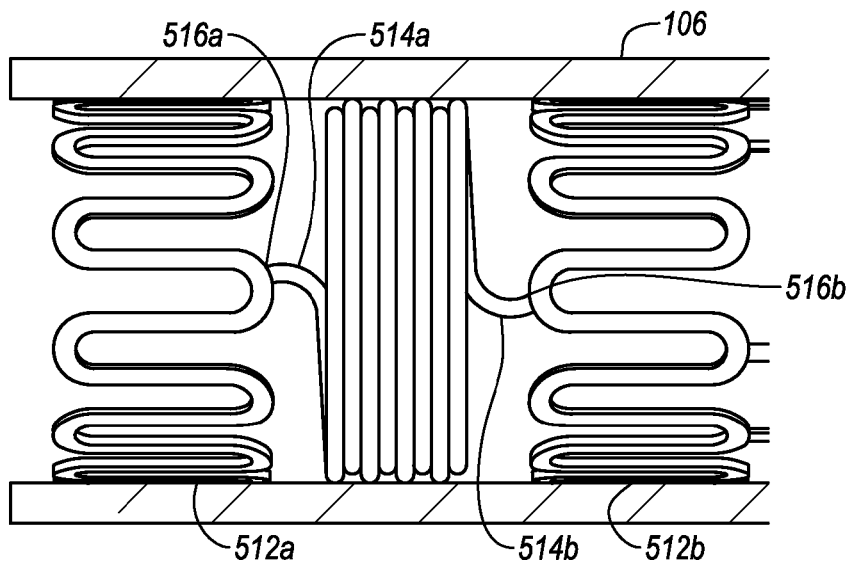
FIG. 5D illustrates a close-up view of the example embodiment of a medical device shown in FIGS. 5A through 5C.

In one example embodiment, and as illustrated in FIGS. 5B through 5C, the coil coupling elements 514a and 514b are configured to expand. In particular, just as the first and second segments 512a and 512b expand upon deployment, the coil coupling elements 514a and 514b may also expand upon deployment. The expanding motion may act to decouple the coil coupling elements 514a and 514b. For example, FIG. 5B illustrates the vascular endoprosthesis 500 at a stage where the first segment 512a is deployed from the delivery sheath 106 and is expanding radially. Moreover, the coil coupling elements 514a and 514b are also shown expanding radially, since they too have been deployed from the delivery sheath 106. In FIG. 5C, the first segment 512a, and the coil coupling elements 514a and 514b, have radially expanded to engage the body lumen 102. Upon the expansion, the coil coupling elements 514a and 514b may be configured to decouple, as illustrated in FIG. 5C.

In another example, the coil coupling elements 514a and 514b may not expand radially; however, the coil coupling elements may still decouple upon the radial expansion of the first segment 512a. As can be understood, since the "jumping" force is generally directed parallel to the body lumen 102 path, the coil coupling elements 514a and 514b are able to remain connected and thus maintain a specified distance between the first and second segments 512a and 512b. Upon further radial expansion of first segment 512a, however, the coil coupling elements 514a and 514b are permitted to release from one another because the radial expansion of the first segment 512a in relation to the static radial position of the second segment 512b pulls in a direction generally perpendicular to the body lumen 102 path, and thus in a direction that allows the coil coupling elements 514a and 514b to decouple. In particular, as first segment 512a expands, the coil coupling element 514a is allowed to laterally slip out of connection or release from coil coupling element 514b.

As has been discussed with previous embodiments, the configuration of the coil coupling elements 514a and 514b illustrated in FIGS. 5A through 5D may be such that upon full deployment of the first and second segments 512a and 512b, the coil coupling elements 514a and 514b may still be interconnected or partial interconnected. In this case, the coil coupling elements 514a and 514b may be made from a bioerodible, bioabsorbable, biodegradable, or bioresorbable material such that the coil coupling elements 514a and 514b dissolve and create completely decoupled, segmented vascular endoprosthesis in the deployed configuration. Likewise, the coil coupling elements 514a and 514b may be made from a SMA material such that the coil coupling elements 514a and 514b may transition from a coupled configuration to a released configuration upon a transition in temperature. For example, the coil coupling elements may be configured to transition from a coil to a substantially straight member upon a transition in temperature.

Figure 6A:
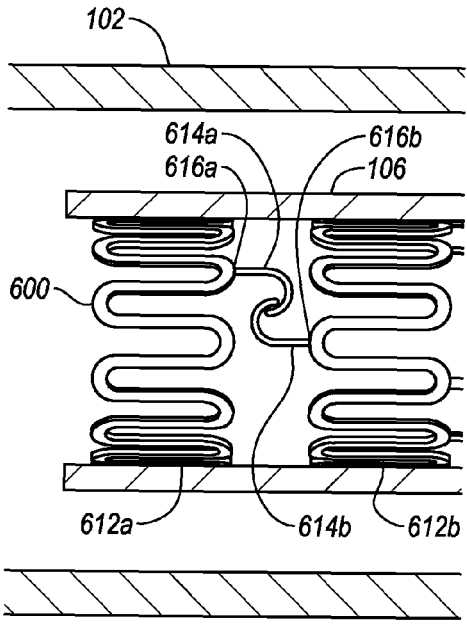
FIG. 6A through 6C illustrate a cross-sectional view of an example medical device at various stages of an example deployment.
Figure 6B:
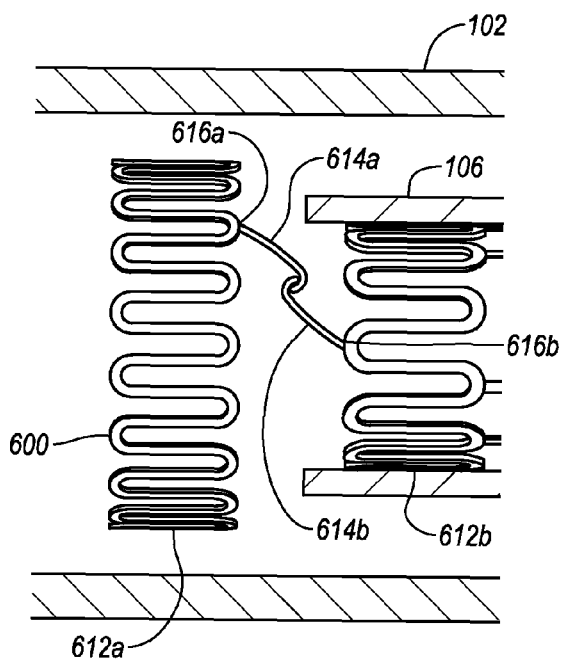

FIG. 6A illustrates yet another example embodiment of a vascular endoprosthesis 600. In particular, the vascular endoprosthesis 600 includes at least a first segment and a second segment 612a and 612b. The first and second segments 612a and 612b are illustrated in the delivery configuration in FIG. 6A, and are interconnected or coupled together by hook coupling elements 614a and 614b. Similar to the previously discussed embodiments, the hook coupling elements 614a and 614b may be configured to decouple upon being deployed into a deployed configuration.

Figure 6C:
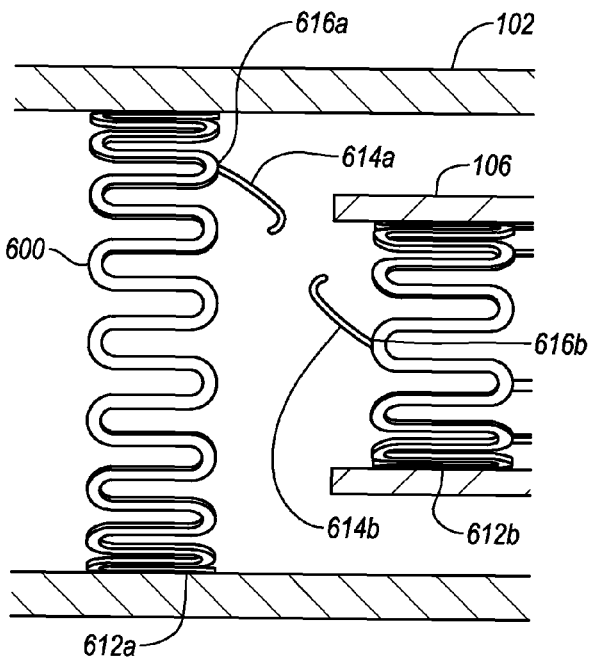

For instance, as the vascular endoprosthesis 600 is deployed from the delivery sheath 106, the first segment 612a exits the delivery sheath 106 and begins to expand towards the body lumen 102 wall. Upon initial expansion, the hook coupling elements 614a and 614b remain coupled together, thus reducing or eliminating the potential of segment 612a from "jumping" out of the delivery sheath 106. As the first segment 612a continues to radially expand towards the body lumen 102 wall, as shown in FIG. 6C, the hook coupling elements 614a and 614b become uncoupled, such that first segment 612a is now a stand-alone segment within the body lumen.

As with previously discussed embodiments, the hook coupling elements 614a and 614b may be made out of bioerodible, bioabsorbable, biodegradable, or bioresorbable material such that if the hook coupling elements 614a and 614b are configured to remain coupled after full deployment and full expansion of each segment, then the hook coupling elements 614a and 614b may dissolve within the body lumen 102, thus, leaving a segmented and decoupled vascular endoprosthesis.

In addition to the specific example embodiments discussed above, various other configurations may be used for the coupling elements in order to couple or interconnect the segments of a vascular endoprosthesis. For example, adjacent segments may be coupled together using dissolving coupling elements selected from the group, by way of example only and not limitation, of sleeves, bar joinery elements, blunt joinery elements, overlay joinery elements, complementary male and female joinery elements, ball and socket or complementary finger joinery elements, and combinations thereof. Moreover, a combination of coupling elements may be used between one segment to the next and/or between two adjacent segments of a vascular endoprosthesis.

One of the advantages of forming a vascular endoprosthesis using coupling elements to couple a number of segments is that the vascular endoprosthesis may be customizable to a particular treatment application or to a particular patient's needs by choosing segments with different configurations. For example, configurations may include at least one of material composition, thickness, flexibility, shape, structure, shape memory, austenite finish temperature, or radial force.

Figure 7:
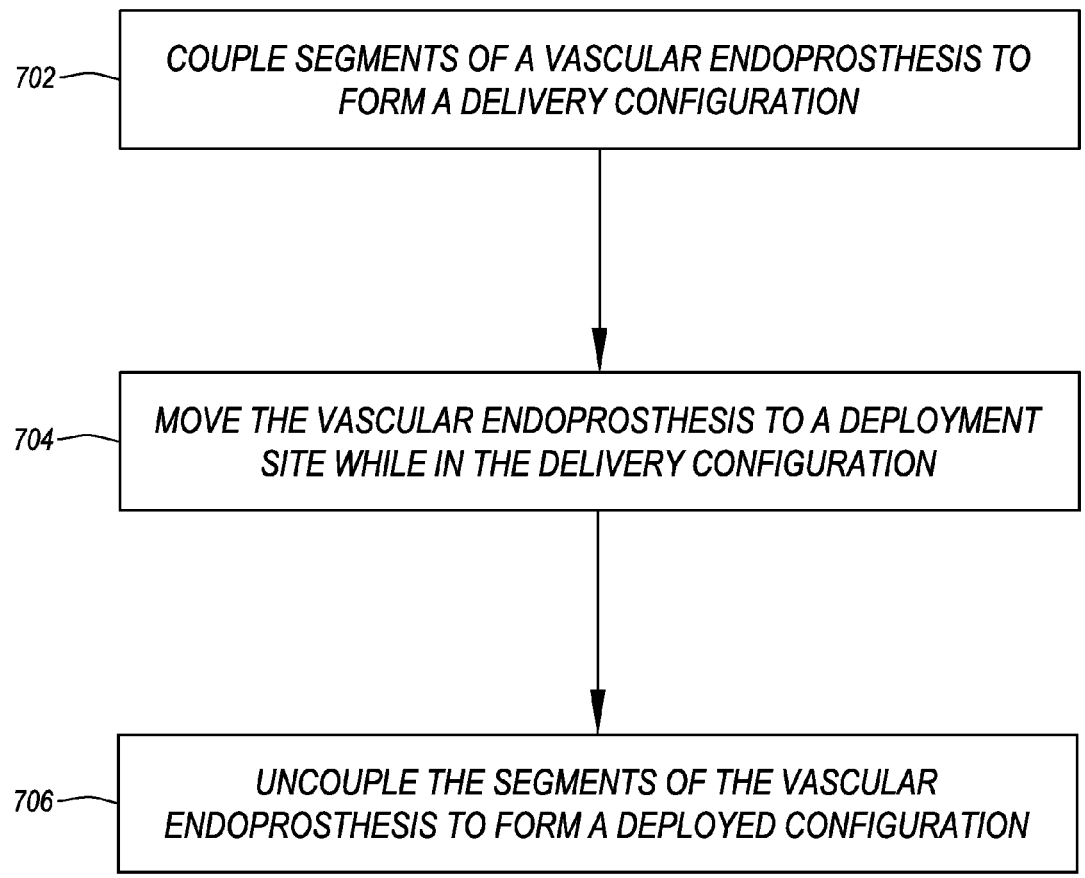
FIG. 7 illustrates an example method of placing an example medical device.

Accordingly, the previous figures and the corresponding text provide a number of different components and systems that may be used to place a vascular endoprosthesis in a body lumen. In addition to the foregoing, other example embodiments may also be described in terms of flowcharts comprising one or more acts in a method for accomplishing a particular result. For example, FIG. 7 illustrates a method of placing a segmented vascular endoprosthesis inside a body lumen. The elements of FIG. 7 are discussed more fully below with respect to the disclosures of FIGS. 1 through 6.

For example, FIG. 7 shows that a method in accordance with an example implementation of the invention may include an element 702 of coupling segments of a vascular endoprosthesis to form a delivery configuration. Element 702 may involve coupling segments of the segmented vascular endoprosthesis together to form a delivery configuration. For example, as shown in FIG. 2, the segments 212 may be coupled together using coupling elements as described herein. Coupling the coupling segments may occur as the segments are compressed or placed into the delivery configuration.

Similarly, FIG. 7 illustrates an element 704 of moving the vascular endoprosthesis to a deployment site while the vascular endoprosthesis is in the delivery configuration. Element 704 may involve moving the segmented vascular endoprosthesis to a deployment site while in the delivery configuration. For example, FIG. 1A illustrates that the vascular endoprosthesis 110 is moved to a deployment site using a delivery sheath 106 that follows a guide wire 104.

FIG. 7 also illustrates that a method in accordance with an example embodiment of the present invention may comprise an element 706 of uncoupling or disengaging the segments of the vascular endoprosthesis to place the vascular endoprosthesis in a deployed configuration. Element 706 may involve uncoupling the segments of the segmented vascular endoprosthesis to form the deployed configuration. For example, FIG. 1B illustrates a vascular endoprosthesis 110 that is in a deployed configuration and that no longer has coupling elements, but rather the segments 112 are uncoupled within the body lumen 102.

II. Endoprosthetic Composition

The above disclosed examples of a vascular endoprosthesis may be made from a variety of materials, such as, but not limited to, those materials which are well known in the art of vascular endoprosthesis manufacturing. This may include, but is not limited to, a vascular endoprosthesis having a primary material for both the segments and the coupling elements. Alternatively, the coupling elements may be made from material different from the segments. Generally, the materials for the vascular endoprosthesis may be selected according to the structural performance and biological characteristics that are desired.

In one configuration, the coupling elements and/or the segments may have multiple layers, with at least one layer being applied to a primary material. The multiple layers on the coupling elements and/or the segments may be resiliently flexible materials or rigid and inflexible materials. For example, materials such as Ti3Al2.5V, Ti6Al4V, 3-2.5Ti, 6-4Ti and platinum may be particularly good choices for adhering to a flexible material, such as, but not limited to, Nitinol and providing good crack arresting properties. The use of resiliently flexible materials may provide shock-absorbing characteristics to the coupling elements, and/or segments, which may also be beneficial for absorbing stress and strains, which may inhibit crack formation at high stress zones. Also, the multiple layers may be useful for applying radiopaque materials to the vascular endoprosthesis.

Self-expanding embodiments of a vascular endoprosthesis may include a material made from any of a variety of known suitable materials, such as a shaped memory material ("SMM"). For example, the SMM may be shaped in a manner that allows for restriction to induce a substantially tubular, linear orientation while within a delivery sheath, but may automatically retain the memory shape of the vascular endoprosthesis once deployed from the delivery sheath. SMMs have a shape memory effect in which they may be made to remember a particular shape. Once a shape has been remembered, the SMM may be bent out of shape or deformed and then returned to its original shape by unloading the material from strain or heating. Typically, SMMs may be shape memory alloys ("SMA") comprised of metal alloys, or shape memory plastics ("SMP") comprised of polymers.

Usually, an SMA may have any non-characteristic initial shape that may then be configured into a memory shape by heating the SMA and configuring the SMA into the desired memory shape. After the SMA is cooled, the desired memory shape may be retained. This allows for the SMA to be bent, straightened, compacted, and placed into various contortions by the application of requisite forces; however, after the forces are released, the SMA may be capable of returning to the memory shape. The main types of SMAs are as follows: copper-zinc-aluminium; copper-aluminium-nickel; nickel-titanium ("NiTi") alloys known as nitinol; and cobalt-chromium-nickel alloys or cobalt-chromium-nickel-molybdenum alloys known as elgiloy alloys. The temperatures at which the SMA changes its crystallographic structure are characteristic of the alloy, and may be tuned by varying the elemental ratios.

In one example, the primary material of a vascular endoprosthesis may be a NiTi alloy that forms superelastic nitinol. In the present case, nitinol materials may be trained to remember a certain shape, straightened in a delivery sheath, such as a catheter, or other tube, and then released from the delivery sheath to return to its trained shape. Also, additional materials may be added to the nitinol depending on a desired characteristic.

An SMP is a shape-shifting plastic that may be fashioned into a vascular endoprosthesis in accordance with the present invention. It may be beneficial to include at least one layer of an SMA and at least one layer of an SMP to form a multilayered body; however, any appropriate combination of materials may be used to form a multilayered vascular endoprosthesis. When an SMP encounters a temperature above the lowest melting point of the individual polymers, the blend makes a transition to a rubbery state. The elastic modulus may change more than two orders of magnitude across the transition temperature ("Ttr"). As such, an SMP may be formed into a desired shape of a vascular endoprosthesis by heating it above the Ttr, fixing the SMP into the new shape, and cooling the material below Ttr. The SMP may then be arranged into a temporary shape by force, and then resume to the memory shape once the force has been removed. Examples of SMPs include, but are not limited to, biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP may be used in accordance with the present invention.

For example, VERIFLEX, the trademark for CRG's family of shape memory polymer resin systems, currently functions on thermal activation which may be customizable from −20° F. to 520° F., allowing for customization within the normal body temperature. This allows a vascular endoprosthesis having at least one layer comprised of VERIFLEX to be inserted into a delivery sheath. Once unrestrained by the delivery sheath, the body temperature may cause the vascular endoprosthesis to return to its functional shape. The coupling elements and the struts in the coupling segments may be formed of different materials or be formed from a different and/or overlapping set of materials or alloys such that they respond to temperature differently. Thus, the coupling segments may disengage or decouple during deployment without impacting the shape memory of the struts or of the coupling segments.

A vascular endoprosthesis having at least one layer made of an SMM or suitable superelastic material and other suitable layers may be compressed or restrained in its delivery configuration within a delivery device using a sheath or similar restraint, and then deployed to its desired configuration at a deployment site by removal of the restraint as is known in the art. A vascular endoprosthesis made of a thermally-sensitive material may be deployed by exposure of the vascular endoprosthesis to a sufficient temperature to facilitate expansion as is known in the art.

Balloon-expandable vascular endoprosthesis embodiments may be comprised of a variety of known suitable deformable materials, including stainless steel, silver, platinum, tantalum, palladium, cobalt-chromium alloys or other known biocompatible materials.

For delivery, the balloon-expandable vascular endoprosthesis having suitable materials may be mounted in the delivery configuration on a balloon or similar expandable member of a delivery device. Once properly positioned within the body lumen at a desired location, the expandable member may be expanded to expand the vascular endoprosthesis to its deployed configuration as is known in the art.

Also, balloon vascular endoprosthesis embodiments may include a suitable biocompatible polymer in addition to or in place of a suitable metal. The polymeric vascular endoprosthesis may include biodegradable or bioabsorbable materials, which may be either plastically deformable or capable of being set in the deployed configuration. If plastically deformable, the material may be selected to allow the vascular endoprosthesis to be expanded in a similar manner using an expandable member so as to have sufficient radial strength and scaffolding and also to minimize recoil once expanded. If the polymer is to be set in the deployed configuration, the expandable member may be provided with a heat source or infusion ports to provide the required catalyst to set or cure the polymer. Alternative known delivery devices and techniques for self-expanding endoprostheses likewise may be used.

Additionally, a self-expanding configuration of a vascular endoprosthesis may include a biocompatible material capable of expansion upon exposure to the environment within the body lumen. Examples of such biocompatible materials may include a suitable hydrogel, hydrophilic polymer, biodegradable polymers, bioabsorbable polymers. Examples of such polymers may include poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly (beta-hydroxybutyrate), polyhydroxybutyrate-hydroxyvaleric acids, combinations thereof, or the like. For example, a self-expandable vascular endoprosthesis may be delivered to the desired location in an isolated state, and then exposed to the aqueous environment of the body lumen to facilitate expansion.

Furthermore, the vascular endoprosthesis may be formed from a ceramic material. In one aspect, the ceramic may be a biocompatible ceramic which optionally may be porous. Examples of suitable ceramic materials include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic may be provided as sinterable particles that are sintered into the shape of a vascular endoprosthesis or layer thereof.

Moreover, the vascular endoprosthesis may include a radiopaque material to increase visibility during placement. Optionally, the radiopaque material may be a layer or coating on any portion of the vascular endoprosthesis. The radiopaque materials may be platinum, tungsten, silver, stainless steel, gold, tantalum, bismuth, barium sulfate, or a similar material.

A. Biodegradable Coating Layers

It is further contemplated that the external surface and/or internal surface of the vascular endoprosthesis (e.g., exterior and luminal surfaces) may be coated with another material having a composition different from the primary endoprosthetic material. The use of a different material to coat the surfaces may be beneficial for imparting additional properties to the vascular endoprosthesis, such as providing radiopaque characteristics, drug-reservoirs, and improved biocompatibility.

In one configuration, the external and/or internal surfaces of a vascular endoprosthesis may be coated with a biocompatible material. Such coatings may include hydrogels, hydrophilic and/or hydrophobic compounds, and polypeptides, proteins or amino acids or the like. Specific examples may include polyethylene glycols, polyvinylpyrrolidone ("PVP"), polyvinylalcohol ("PVA"), parylene, heparin, phosphorylcholine, or the like. A preferred coating material may include phosphorylcholine, as disclosed in U.S. Pat. No. 6,015,815 entitled "TETRAZOL-CONTAINING RAPAMYCIN ANALOGS WITH SHORTENED HALF-LIVES," the entirety of which is herein incorporated by reference.

The coatings may also be provided on the vascular endoprosthesis to facilitate the loading or delivery of beneficial agents or drugs, such as therapeutic agents, pharmaceuticals and radiation therapies. As such, the endoprosthetic material and/or holes may be filled and/or coated with a biodegradable material.

Accordingly, the biodegradable material may contain a drug or beneficial agent to improve the use of the vascular endoprosthesis. Such drugs or beneficial agents may include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors having beneficial genes, genes, siRNA, antisense compounds, oligionucleotides, cell permeation enhancers, and combinations thereof. Another example of a suitable beneficial agent is described in U.S. Pat. No. 6,015,815 and U.S. Pat. No. 6,329,386 entitled "TETRAZOLE-CONTAINING RAPAMYCIN ANALOGS WITH SHORTENED HALF-LIVES," the entireties of which are herein incorporated by reference In one configuration, the external surfaces of a vascular endoprosthesis may include a coating comprised of polytetrafluorethylene ("PTFE"), expanded PTFE ("ePTFE"), Dacron, woven materials, cut filaments, porous membranes, harvested vessels and/or arteries, or other such materials to form a stent graft prosthesis. Similarly, a medical device, such as a valve, a flow regulator or monitor device, may be used with the vascular endoprosthesis, such that the vascular endoprosthesis functions as an anchor for the medical device within the body lumen.

In one configuration, different external surfaces of a vascular endoprosthesis, such as a low stress zone less susceptible to flexing, may be coated with functional layers of an imaging compound or radiopaque material. The radiopaque material may be applied as a layer at low stress zones of the vascular endoprosthesis. Also, the radiopaque material may be encapsulated within a biocompatible or biodegradable polymer and used as a coating. For example, the suitable radiopaque material may be palladium platinum, tungsten, silver, stainless steel, gold, tantalum, bismuth, barium sulfate, or a similar material. The radiopaque material may be applied as layers on selected surfaces of the vascular endoprosthesis using any of a variety of well-known techniques, including cladding, bonding, adhesion, fusion, deposition or the like.

B. Matrix with Crack-Inhibiting Features

In addition to the foregoing compositions, a crack-inhibiting feature may be included within the material matrix of the vascular endoprosthesis. Exemplary crack-inhibiting features may include holes, fibers, particles, and bodies having multiple layers, such as planar layers or concentric layers. As such, any of the foregoing compositions may be impregnated and/or encapsulated with a suitable fibrous or particulate material. Also, a vascular endoprosthesis may be prepared to include a plurality of holes that extend through the endoprosthetic body. Moreover, the endoprosthetic body may have multiple layers separated by junctions or boundaries that inhibit crack propagation.

III. Method of Making Endoprostheses

Various different manufacturing techniques are well known and may be used for fabrication of the segmented vascular endoprosthesis of the present invention. For example, the vascular endoprosthesis may be formed from a hollow tube using a known technique, such as laser cutting, EDM, milling, chemical etching, hydro-cutting, and the like. Also, the vascular endoprosthesis may be prepared to include multiple layers or coatings deposited through a cladding process such as vapor deposition, electroplating, spraying, or similar processes. Also, various other processes may be used such as those described below and or others known to those skilled in the art in light of the teaching contained herein.

Optionally, the vascular endoprosthesis may be fabricated from a sheet of suitable material, where the sheet is rolled or bent about a longitudinal axis into the desired tubular shape. Additionally, either before or after being rolled into a tube, the material may be shaped to include endoprosthetic elements by being shaped with well-known techniques such as laser-cutting, milling, etching or the like. If desired, the lateral edges of the structure may be joined together, such as by welding or bonding, to form a closed tubular structure, or the lateral edges may remain unattached to form a coiled, rolled sheet or open tubular structure. Such fabrication techniques are described in more detail below.

A. Sintering

A method of making a vascular endoprosthesis in accordance with the present invention may include sintering sinterable particles to provide a sintered article having the shape of the vascular endoprosthesis. The sintering may be conducted in molds that are in the shape of a vascular endoprosthesis.

In one configuration, the sintered body may be obtained from a molded green body prepared by molding a mixture of sinterable particles with or without a binder into the shape of a vascular endoprosthesis or body intermediate. Sintering a molded green body that has the shape of a vascular endoprosthesis may provide a sintered body that may function as a vascular endoprosthesis with no or minimal additional processing. Alternatively, after the green body has been formed in the mold and sintered into a hardened vascular endoprosthesis, the process may include shaping the sintered body with a stream of energy and/or matter in order to obtain a desired shape. Thus, sintering a green body in a mold may result in a vascular endoprosthesis that is either ready for use, or requires additional processing or finishing.

Additionally, the sintered body may be shaped into a vascular endoprosthesis as described herein. Also, the vascular endoprosthesis may be further processed after sintering and/ or shaping such as by grinding, sanding, or the like to provide enhanced surface characteristics.

B. Drawing Concentric Tubes

In one configuration, a multilayered vascular endoprosthesis in accordance with the present invention may be prepared by a drawing process that draws two or more distinct concentric tubes into a single tube having two or more layers. Additionally, such a drawing process may combine multiple concentric tubes into a single multilayered tube. The drawing process may be configured to produce junctions separating adjacent layers or bonds that bond adjacent layers. As such, the sequentially-adjacent concentric tubes may be drawn together and progressively reduced in a cross-sectional profile until the desired size and residual clamping stress is attained.

Accordingly, a metallurgical bond may be prepared with elements of each sequentially-concentric tube diffusing together and bonding so as to form a strong metallurgical bond. Such a metallurgical bond may be achieved by applying significant pressure and heat to the tubes. As such, a metallurgical bond may form a diffusion layer at the interface between sequentially-adjacent concentric tubes (i.e., layers). The characteristics of these diffusion layers may be controlled by the proper heat treatment cycle. In part, this is because the heat treatment, temperature, and time of processing may control the rates of transfer of the diffusing elements that produce the diffusion layers. Also, the pressure at the interface between layers may be developed so as to result in the residual radial clamping stress in the tube after drawing.

In one example of this process, an outer tube of nitinol, a middle tube of tantalum, and an inner tube of Nitinol may be arranged to form the composite structure. The multilayered material may be produced to result in bonding between the layers so as to achieve a residual clamping stress of about 50 p.s.i. Accordingly, the annealing process may be performed within a limited range of time and temperatures. For example, the lower limit may be at least about 1550° F. for about six minutes, and the upper limit may be about 1850° F. for about 15 minutes.

In another configuration, a metallic interleaf layer may be placed between separate tubes so as to bond the tubes together and form a multilayered material. The multiple tubes separated by the metallic interleaf layer may be drawn together and progressively reduced until the desired cross-sectional profile and residual clamping stress is attained, as described above. The drawn tubes may be heat-treated to form a diffusion bond between the separate layers. As such, the metallic interleaf layer may enhance the diffusion rate or type of diffusing atoms that are transported across a diffusion region between one layer and the interleaf layer.

In one configuration, a multilayered sheet may be prepared to have separate layers of different materials or the same material. For example, the multilayered sheet may have a top layer of nitinol, a middle layer of tantalum, and a bottom layer of Nitinol. The sheet may be prepared by metallurgically bonding the layers prior to a deep drawing process, which is well known in the art. During the deep drawing process, the sheet may be placed over a die and forced into the die, such as by a punch or the like. A tube having a closed end and a defined wall thickness may be formed in the die. This process may be repeated using a series of dies that have progressively decreasing diameters until a multilayered tube is formed having the desired diameter and wall thickness. For certain material combinations, intermediate heat treatments may be performed between the progressive drawing operations to form a multilayered material that is resistant to delaminating. Once a multilayered tube of desired thickness and dimensions has been formed, the closed end and the curved edges may be cut off. Then, the tube may be heat treated, as described above, until proper inter-metallic bonds are formed between the layers.

C. Shaping

Accordingly, an endoprosthetic material may be shaped by various methods as described in more detail below. Such shaping techniques may utilize streams of energy and/or streams of matter in order to impart shapes into the endoprosthetic material. The streams of energy include photons, electromagnetic radiation, atomic, and sub-atomic materials, as described above. On the other hand, the streams of matter are considered to include materials larger than atomic scale particles, and may be microscopic or macroscopic in size. In any event, the shaping may be designed to direct a stream of energy or a stream of matter at the endoprosthetic material to form an endoprosthetic element and/or holes therein.

In one configuration, a stream of energy may cut, shape, and/or form a tube into an endoprostheses by generating heat at the site where the stream intersects the material, as is well known in the art. The thermal interaction may elevate the local temperature to a point, which may cut, melt, shape, and/or vaporize portions of the endoprosthetic material from the rest of the material.

Accordingly, one configuration of the stream-cutting apparatus may operate and shape the endoprosthetic material by thermal interactions. As such, any of the thermal processes described herein may be used for thermal-cutting. For example, such thermal interactions may arise from laser beam treatment, laser beam machining, electron beam machining, electrical discharge machining, ion beam machining, and plasma beam machining.

In one configuration, by knowing the thermal properties of the endoprosthetic material, precise energy requirements may be calculated so that the thermal beam provides the appropriate or minimum energy for melting and/or vaporizing the material without significantly melting undesirable portions of the material. For example, laser beams are a common form of a stream of energy that may be used to shape the endoprosthetic material. Additionally, there are instances where a laser is preferred over all other cutting techniques because of the nature of the resulting vascular endoprosthesis as well as the characteristics of the endoprosthetic material.

In one configuration, a vascular endoprosthesis may be manufactured as described herein using a femtosecond laser. A femtosecond laser may be desirable in producing a vascular endoprosthesis in accordance with the multilayered composite structure of the present invention because it produces a smaller heat influence zone ("HIZ") or heat affected zone (HAZ) compared to other lasers, or it may substantially eliminate the HIZ or HAZ. In comparison, cutting a vascular endoprosthesis using known methods may result in the tubular material being melted away, and thereby forming the pattern in the tubular member. Such melting may result in embrittlement of some materials due to oxygen uptake into the HIZ.

In one configuration, electrical discharge machining is used to shape endoprosthetic material and/or form holes in the endoprosthetic material as desired. As such, electrical discharge machining may be capable of cutting all types of conductive materials such as exotic metal including titanium, hastaloy, kovar, inconel, hard tool steels, carbides, and the like. In electrical discharge, the main interaction between the stream of energy and the endoprosthetic material is thermal, where heat is generated by producing electrical discharges. This may lead to the endoprosthetic material being removed by melting and evaporation. Some examples of electrical discharge machining include wire electron discharge machining, CNC-controlled electrical discharge machining, sinker electrical discharge machining, small hole discharge machining, and the like.

In another configuration, a charged particle beam may be used for shaping the endoprosthetic material, wherein electron beams and ion beams exemplify charged particle beams. A charged particle beam is a group of electrically-charged particles that have approximately the same kinetic energy and move in approximately the same direction. Usually, the kinetic energies are much higher than the thermal energies of similar particles at ordinary temperatures. The high kinetic energy and the directionality of these charged beams may be useful for cutting and shaping of the green bodies, as described herein. Additionally, there are some instances where electron beams or ion beams are preferred over other cutting techniques.

In one configuration, a stream of chemical matter may be used in order to shape or form holes in the endoprosthetic material. Chemical-jet milling, for example, provides selective and controlled material removal by jet and chemical action. As such, the process is similar to water-jet cutting, which is described in more detail below. In any event, chemical-jet milling may be useful for shaping various types of endoprosthetic materials, which provides intricate shaping capabilities.

In another configuration, electrochemical shaping may be based on a controlled electrochemical dissolution process similar to chemical-jet milling an endoprosthetic material. As such, the endoprosthetic material may be attached to an electrical source in order to allow an electrical current to assist in the shaping.

In one configuration, hydro-cutting or water-jet cutting may be used to shape an endoprosthetic material. Hydro-cutting is essentially a water-jet technology that uses the high force and high pressure of a stream of water directed at the endoprosthetic material in order to cut and shape the material as desired. Hydro-cutting may be preferred over some of the other stream-cutting technologies because it may be free of heat, flame, and chemical reactions, and may provide a precise cold shaping technique. Also, heated water with or without being doped with reactive chemicals may also be used. Hydro-cutting is particularly suitable for polymeric endoprostheses, but may be used for metal materials when combined with abrasive particles, as described below.

Additionally, hydro-cutting may be enhanced by the introduction of particulate materials into the water feed line. As such, some hydro-cutting techniques utilize garnet or other rigid and strong materials in order to apply an abrasive cutting force along with the force applied by the water itself. Also, the hydro-cutting process in the present invention may be used with or without inclusion of such abrasives.

Additionally, one of the benefits of hydro-cutting is the ability to reutilize and recycle the spent water-jet material. As such, the endoprosthetic material may be easily separated from the spent water, thereby enabling the recycling and reuse of the water during the hydro-cutting process.

In one configuration, sandblasting, which fits into the regime of stream of matter cutting, may be used to shape an endoprosthetic material by projecting a high energy stream of sand particles at the material. Sandblasting cuts materials in a manner similar to hydro-cutting, especially when the water-jet is doped with abrasive particulates. Additionally, various other particulate streams other than sand may be used in the stream-cutting techniques and machinery.

D. Additional Processing

An additional step of passivation may be performed during the manufacturing stage of the vascular endoprosthesis in order to form a homogeneous oxide layer for corrosion-resistance. The passivation process may be performed prior to installation of the markers in accordance with the present invention or it may be performed after installation of the radiopaque markers. Alternatively, multiple passivation processes may be performed, once prior to application of the markers, and again after insertion of the markers.

As originally shaped and/or fabricated, the vascular endoprosthesis may correspond to its delivery configuration, to a deployed configuration, or to a configuration therebetween. The vascular endoprosthesis may be fabricated with a configuration at least slightly larger than the delivery configuration. In this manner, the vascular endoprosthesis may be crimped or otherwise compressed into its delivery configuration in a corresponding delivery device.

In another configuration, the vascular endoprosthesis may be originally fabricated from a tube having a diameter corresponding to the deployed configuration. In this manner, the longitudinally-free portions of the segments (e.g., elbow or foot not at a connection location) and circumferentially-free portions (e.g., the toe and/or heel portion of the foot extensions) may be maintained within the general cylindrical shape (e.g., diameter) of the vascular endoprosthesis when deployed, so as to avoid such portions from extending radially inward when in the deployed configuration. The vascular endoprosthesis may be designed to match the target vessel in which the vascular endoprosthesis is to be deployed. For example, a stent may be provided with an outer diameter in the deployed configuration ranging from about 1 mm for neurological vessels to about 25 mm for the aorta. Similarly, a stent may be provided with a length ranging from about 5 mm to about 200 mm. Variations of these dimensions will be understood in the art based upon the intended application or indication for the vascular endoprosthesis.

Also, the geometry of each component of the vascular endoprosthesis or endoprosthetic element, such as the width, thickness, length and shape of the strut elements, coupling elements, crossbars, connectors, elbows, foot portions, ankle portions, toe portions, heel portions and the like may be selected to obtain predetermined expansion, flexibility, foreshortening, coverage scaffolding, and cross-sectional profile characteristics. For example, longer crossbars and/or connectors may promote greater radial expansion or scaffolding coverage. The phase difference or circumferential alignment between adjacent segments likewise may be altered to control coverage and flexibility. Similarly, the number and placement of coupling locations and, if present, the coupling elements, between longitudinally-adjacent segments may be selected to obtain the desired flexibility of the vascular endoprosthesis. The number of elbows and/or foot extensions between coupling locations also may be varied to achieve desired performance characteristics.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A vascular endoprosthesis comprising:
    a radially expandable first segment having a proximal end and a distal end;
    a radially expandable second segment having a proximal end and a distal end;
    a first spiral coupling element extending from said proximal end of said first segment toward said distal end of said second segment; and
    a second spiral coupling element extending from said distal end of said second segment toward said proximal end of said first segment, wherein said first spiral coupling element and said second spiral coupling element couple said first segment and said second segment when in a delivery configuration, and wherein said first spiral coupling element and said second spiral coupling element decouple when said first segment and said second segment are in a deployed configuration, wherein the first segment is deployed before the second segment and wherein the first spiral coupling element and the second spiral coupling element remain coupled during deployment of the first segment, wherein said first spiral coupling element uncoils and disconnects to release from said second spiral coupling element by a distance in a longitudinal direction of the vascular endoprosthesis.

2. The vascular endoprosthesis as recited in claim 1, wherein said first and second spiral elements are operatively associated with each other by coiling together, and where said first and second spiral elements are disassociated with each other by uncoiling from each other.

3. The vascular endoprosthesis as recited in claim 1, wherein said first and second spiral elements have cross-sectional profiles that include side walls that are angled, wherein said angle on said first spiral element is complementary to said angle on said second spiral element.

4. The vascular endoprosthesis as recited in claim 1, wherein said first and second spiral coupling elements are made from a material that is bioabsorbable, bioresorbable, biodegradable, or bioerodible.

5. The vascular endoprosthesis as recited in claim 1, wherein said first and second spiral coupling elements are made from a shape memory material, the first and second spiral coupling elements cooperating to couple said first and second segments in a first phase of said shape memory, and the first and second coupling elements cooperating to decouple said first and second segments in a second phase of said shape memory material.

6. The vascular endoprosthesis as recited in claim 5, wherein said first phase of said shape memory material corresponds with said delivery configuration, and wherein said second phase of said shape memory material corresponds with said deployed configuration.

7. A vascular medical device, comprising:
    a first annular segment and a second annular segment, the first annular segment and the second annular segment being radially expandable; and
    at least one pair of spiral coupling elements disposed on said first and second annular segments, said at least one pair of spiral coupling elements operatively associated with one another to couple said first and second annular segments together until said first and second annular segments undergo a transition from a delivery configuration towards a deployed configuration, wherein the first annular segment is deployed before the second annular element, wherein each pair of spiral coupling elements remain coupled when deploying the first annular segment and are uncoupled after deployment of the first annular segment, wherein said first spiral coupling element uncoils and disconnects to release from said second spiral coupling element by a distance in a longitudinal direction of the vascular endoprosthesis.

8. The vascular medical device as recited in claim 7, wherein said transition occurs between an initial radial expansion of said first annular segment and a full radial expansion of said first annular segment, and when said second annular segment has not radially expanded.

9. The vascular medical device as recited in claim 7, wherein said at least one pair of coupling elements are made from a shape memory material and are caused to change from a first shape that facilitates coupling to a second shape that facilitates decoupling.

10. The vascular medical device as recited in claim 7, wherein at least a portion of said at least one pair of spiral coupling elements is made from a dissolvable material that is bioabsorbable, bioresorbable, biodegradable, or bioerodible.

11. The vascular medical device as recited in claim 6, wherein said at least one pair of spiral coupling elements are configured to provide a defined spacing between said first annular segment and second annular segment after said first and second annular segments are deployed.

12. A medical device system, comprising:
a tubular delivery sheath having a proximal end and a distal end;
a vascular endoprosthesis having a delivery configuration and a deployed configuration, wherein a first segment and a second segment are coupled in said delivery configuration and decoupled in said deployed configuration, wherein said first segment is deployed before said second segment and wherein said second segment remains coupled to said first segment during deployment, each of said first segment and said second segment including a spiral coupling element, wherein said spiral coupling element of said first element uncoils and disconnects to release from said spiral coupling element of said second element by a distance in a longitudinal direction of said vascular endoprosthesis; and
an actuator that is operatively associated with said tubular delivery sheath such that said actuator and said delivery sheath cooperate to transition said vascular endoprosthesis from said delivery configuration to said deployed configuration.

13. The medical device system as recited in claim 12, wherein said spiral coupling element of said first segment and said spiral coupling element of said second segment automatically decouple said first segment and said second segment when said vascular endoprosthesis transitions from said delivery configuration to said deployed configuration.

14. The medical device system as recited in claim 12, wherein said first segment and said second element are radially expandable, and said spiral coupling elements decouple during said first segment's radial expansion.

15. A method of placing a segmented vascular endoprosthesis inside a body lumen, comprising:
coupling segments of said segmented vascular endoprosthesis together to form a delivery configuration by operatively associating a first spiral coupling elements with a second spiral coupling element;
moving said segmented vascular endoprosthesis to a deployment site while in said delivery configuration;
deploying the segments one at a time, wherein at least one of the segments remains coupled to the next un-deployed segment via a first and second spiral coupling elements, during deployment of the at least one of the segments; and
uncoupling said segments of said segmented vascular endoprosthesis to form a deployed configuration by uncoiling and disconnecting to release the first spiral coupling element from the second spiral coupling elements by a distance in a longitudinal direction of the segmented vascular endoprosthesis.

16. The method as recited in claim 15, wherein coupling said segments of said segmented vascular endoprosthesis comprises interconnecting two or more spiral coupling elements.

17. The method as recited in claim 16, wherein uncoupling said segments of said segmented vascular endoprosthesis comprises disconnecting said two or more spiral coupling elements.

18. The method as recited in claim 15, further comprising the step of deploying said segmented vascular endoprosthesis at said deployment site within said body lumen before said uncoupling of said segments of said segmented vascular endoprosthesis.

19. The method as recited in claim 18, wherein said two or more spiral coupling elements automatically uncouple upon said deploying of said segmented vascular endoprosthesis.

20. The method as recited in claim 19, wherein said two or more spiral coupling elements are made from a dissolvable material and/or a shape memory material, and wherein the said two or more coupling elements dissolve and/or change shape in order to facilitate the said uncoupling.

* * * * *